(12) United States Patent
Saoji

(10) Patent No.: US 8,788,052 B2
(45) Date of Patent: Jul. 22, 2014

(54) METHODS AND SYSTEMS FOR MINIMIZING A PERCEPTUAL DISTURBANCE CAUSED BY SHORTED ELECTRODES IN AN AUDITORY PROSTHESIS SYSTEM

(75) Inventor: Aniket Saoji, Newhall, CA (US)

(73) Assignee: Advanced Bionics AG, Staefa (CH)

(\*) Notice: Subject to any disclaimer, the term of this patent is extended or adjusted under 35 U.S.C. 154(b) by 0 days.

(21) Appl. No.: 13/983,564

(22) PCT Filed: Jan. 27, 2012

(86) PCT No.: PCT/US2012/022943
§ 371 (c)(1),
(2), (4) Date: Oct. 18, 2013

(87) PCT Pub. No.: WO2012/106207
PCT Pub. Date: Aug. 9, 2012

(65) Prior Publication Data
US 2014/0046402 A1    Feb. 13, 2014

Related U.S. Application Data

(60) Provisional application No. 61/439,554, filed on Feb. 4, 2011.

(51) Int. Cl.
*A61N 1/00* (2006.01)
*A61N 1/36* (2006.01)
*A61N 1/05* (2006.01)

(52) U.S. Cl.
CPC ........... *A61N 1/36032* (2013.01); *A61N 1/0541* (2013.01)
USPC .............................................. 607/57; 607/55

(58) Field of Classification Search
USPC ...................................................... 607/55, 57
See application file for complete search history.

(56) References Cited

U.S. PATENT DOCUMENTS

| | | |
|---|---|---|
| 2007/0225767 A1 | 9/2007 | Daly et al. |
| 2008/0319508 A1 | 12/2008 | Botros et al. |
| 2008/0319509 A1* | 12/2008 | Laback et al. ................... 607/57 |
| 2009/0125081 A1* | 5/2009 | Spitzer et al. ................... 607/55 |

FOREIGN PATENT DOCUMENTS

WO    WO-2009/046502    4/2009

OTHER PUBLICATIONS

International Search Report and Written Opinion received in International Application No. PCT/US12/022943 dated Jun. 8, 2012.

\* cited by examiner

*Primary Examiner* — Nicole F Lavert
(74) *Attorney, Agent, or Firm* — ALG Intellectual Property, LLC

(57) ABSTRACT

An exemplary system for minimizing a perceptual disturbance caused by shorted electrodes in an auditory prosthesis system includes a sound processor configured to determine that a first electrode and a second electrode included in a plurality of electrodes implanted in a patient are shorted together, detect that a main electrical stimulation pulse intended only for the first electrode is to be delivered by an auditory prosthesis to the first electrode, and direct, in response to the detecting, the auditory prosthesis to concurrently deliver the main electrical stimulation pulse to the first electrode and one or more compensating electrical stimulation pulses to one or more additional electrodes included in the plurality of electrodes.

20 Claims, 8 Drawing Sheets

METHODS AND SYSTEMS FOR MINIMIZING A PERCEPTUAL DISTURBANCE CAUSED BY SHORTED ELECTRODES IN AN AUDITORY PROSTHESIS SYSTEM

RELATED APPLICATIONS

The present application claims priority to U.S. Provisional Patent Application No. 61/439,554 by Aniket Saoji, filed on Feb. 4, 2011, and entitled "Methods and Systems for Minimizing a Perceptual Disturbance Caused by Shorted Electrodes in an Auditory Prosthesis System," the contents of which are hereby incorporated by reference in their entirety.

BACKGROUND INFORMATION

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that audio signals reach the cochlea and the hair cells. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous auditory prosthesis systems (e.g., cochlear implant systems) have been developed. Auditory prosthesis systems bypass the hair cells in the cochlea by presenting electrical stimulation directly to the auditory nerve fibers by way of one or more channels formed by an array of electrodes implanted in an auditory prosthesis patient. Direct stimulation of the auditory nerve fibers leads to the perception of sound in the brain and at least partial restoration of hearing function.

Unfortunately, a short may occur between two or more electrodes included in the array of electrodes that are implanted in the auditory prosthesis patient. The shorted electrodes can potentially lead to poor sound quality and/or perceptual disturbances. For example, delivery of an electrical stimulation pulse to a first electrode that is shorted to a second electrode may result in an unwanted electrical stimulation pulse also being delivered to the second electrode. The unwanted electrical stimulation pulse may cause the patient to perceive an unwanted sound.

SUMMARY

An exemplary method of minimizing a perceptual disturbance caused by shorted electrodes in an auditory prosthesis system includes a sound processor determining that a first electrode and a second electrode included in a plurality of electrodes implanted in a patient are shorted together, detecting that a main electrical stimulation pulse intended only for the first electrode is to be delivered by an auditory prosthesis to the first electrode, and directing, in response to the detecting, the auditory prosthesis to concurrently deliver the main electrical stimulation pulse to the first electrode and one or more compensating electrical stimulation pulses to one or more additional electrodes included in the plurality of electrodes. The one or more compensating electrical stimulation pulses are out-of-phase with respect to the unwanted electrical stimulation pulse and are configured to minimize a perceptual disturbance caused by an unwanted electrical stimulation pulse that is delivered to the second pulse as result of the delivery of the main electrical stimulation pulse to the first electrode.

An exemplary sound processor includes a short detection facility configured to determine that a first electrode and a second electrode included in a plurality of electrodes implanted in an auditory prosthesis patient are shorted together and a control facility communicatively coupled to the short detection facility and configured to 1) detect that a main electrical stimulation pulse intended only for the first electrode is to be delivered to the first electrode and 2) direct, in response to the detection, an auditory prosthesis implanted in the patient to concurrently deliver the main electrical stimulation pulse to the first electrode and one or more compensating electrical stimulation pulses to one or more additional electrodes included in the plurality of electrodes. The one or more compensating electrical stimulation pulses are out-of-phase with respect to the unwanted electrical stimulation pulse and are configured to minimize a perceptual disturbance caused by an unwanted electrical stimulation pulse that is delivered to the second pulse as result of the delivery of the main electrical stimulation pulse to the first electrode.

An exemplary auditory prosthesis system includes an auditory prosthesis configured to be implanted within a patient and communicatively coupled to a plurality of electrodes and a sound processor communicatively coupled to the auditory prosthesis. The sound processor is configured to 1) determine that a first electrode and a second electrode included in the plurality of electrodes implanted in the patient are shorted together, 2) detect that a main electrical stimulation pulse intended only for the first electrode is to be delivered to the first electrode, and 3) direct, in response to the detection, the auditory prosthesis to concurrently deliver the main electrical stimulation pulse to the first electrode and one or more compensating electrical stimulation pulses to one or more additional electrodes included in the plurality of electrodes. The one or more compensating electrical stimulation pulses are out-of-phase with respect to the unwanted electrical stimulation pulse and are configured to minimize a perceptual disturbance caused by an unwanted electrical stimulation pulse that is delivered to the second pulse as result of the delivery of the main electrical stimulation pulse to the first electrode.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Methods and systems for minimizing a perceptual disturbance caused by shorted electrodes in an auditory prosthesis system are described herein. As will be described below, the auditory prosthesis system may include an auditory prosthesis (e.g., a cochlear implant), a plurality of electrodes disposed along a lead, and a sound processor. The auditory prosthesis and electrode lead may be implanted within a patient. The sound processor may be located external to the patient (or, in some alternative embodiments, implanted in the patient) and configured to control an operation of the auditory prosthesis.

In some examples, the sound processor may determine that a first electrode and a second electrode included in the plurality of electrodes implanted in the patient are shorted together and detect that a main electrical stimulation pulse intended only for the first electrode is to be delivered by the auditory prosthesis to the first electrode. Because the first and second electrodes are shorted together, delivery of the main electrical stimulation pulse to the first electrode may cause an unwanted electrical stimulation pulse to be simultaneously delivered to the second electrode. To minimize a perceptual disturbance caused by the unwanted electrical stimulation pulse (i.e., one or more sounds that result from delivery of the unwanted electrical stimulation pulse to the second electrode and that may be perceived by the patient), the sound processor may direct the auditory prosthesis to concurrently deliver one or more compensating electrical stimulation pulses to one or more additional electrodes included in the plurality of electrodes when the main electrical stimulation pulse is delivered to the first electrode. As will be described below, the one or more compensating electrical stimulation pulses may be out-of-phase with respect to the unwanted electrical stimulation pulse and may be configured to effectively minimize the perceptual disturbance caused by the unwanted electrical stimulation pulse. In this manner, the undesirable effects of shorted electrodes in an auditory prosthesis system may be automatically minimized or even all together obviated.

Figure 1:
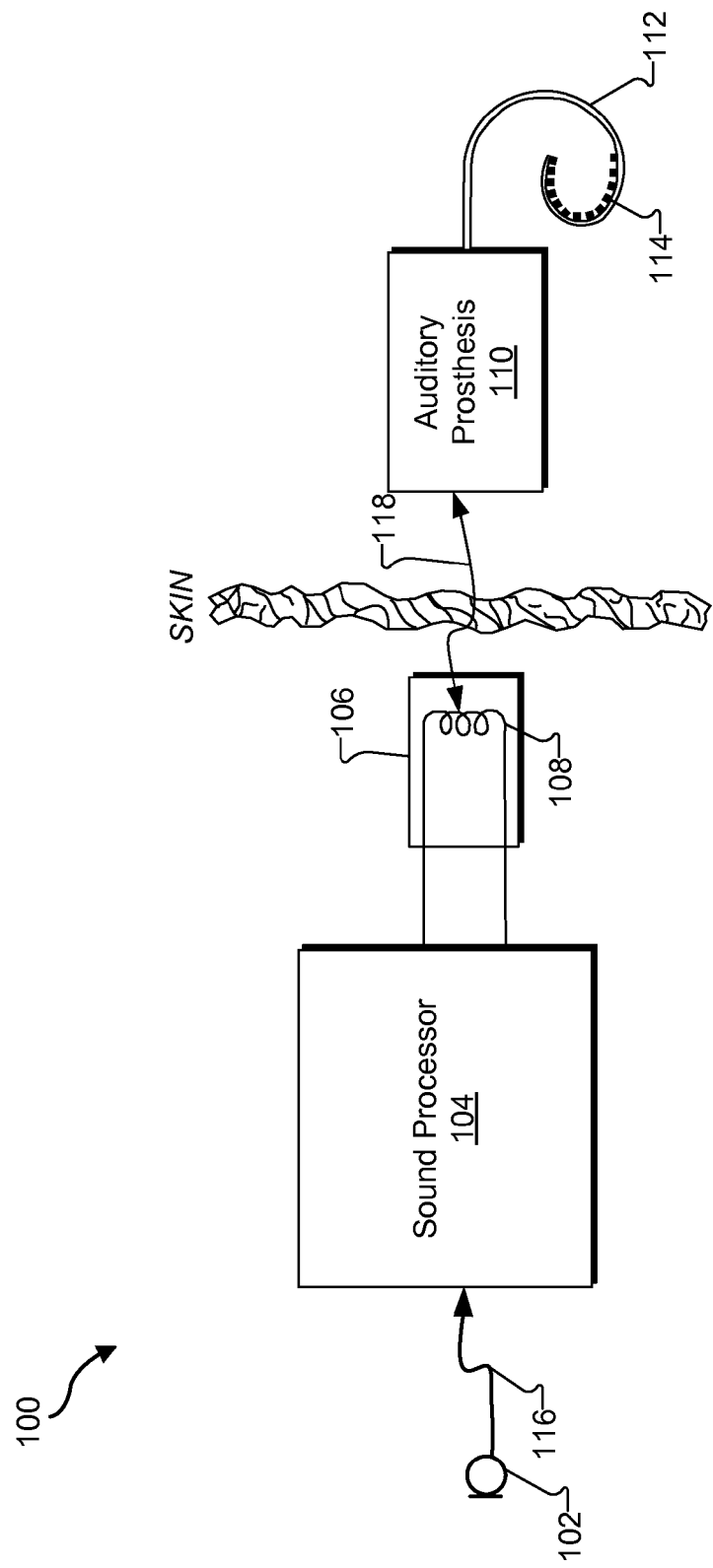
FIG. 1 illustrates an exemplary auditory prosthesis system according to principles described herein.

FIG. 1 illustrates an exemplary auditory prosthesis system 100. Auditory prosthesis system 100 may include a microphone 102, a sound processor 104, a headpiece 106 having a coil 108 disposed therein, an auditory prosthesis 110, and a lead 112 with a plurality of electrodes 114 disposed thereon. Additional or alternative components may be included within auditory prosthesis system 100 as may serve a particular implementation.

As shown in FIG. 1, microphone 102, sound processor 104, and headpiece 106 may be located external to an auditory prosthesis patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct auditory prosthesis 110 to generate and apply electrical stimulation (also referred to herein as "stimulation current") to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the audio signal detected by microphone 102 in accordance with a selected sound processing strategy to generate appropriate stimulation parameters for controlling auditory prosthesis 110. Sound processor 104 may include or be implemented by a behind-the-ear ("BTE") unit, a portable speech processor ("PSP"), and/or any other sound processing unit as may serve a particular implementation. Exemplary components of sound processor 104 will be described in more detail below.

Sound processor 104 may be configured to transcutaneously transmit one or more control parameters and/or one or more power signals to auditory prosthesis 110 with coil 108 by way of a communication link 118. These control parameters may be configured to specify one or more stimulation parameters, operating parameters, and/or any other parameter by which auditory prosthesis 110 is to operate as may serve a particular implementation. Exemplary control parameters include, but are not limited to, stimulation current levels, volume control parameters, program selection parameters, operational state parameters (e.g., parameters that turn a sound processor and/or an auditory prosthesis on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels, channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters. Additional features of sound processor 104 will be described in more detail below.

As shown in FIG. 1, coil 108 may be housed within headpiece 106, which may be affixed to a patient's head and positioned such that coil 108 is communicatively coupled to a corresponding coil included within auditory prosthesis 110. In this manner, control parameters and power signals may be wirelessly transmitted between sound processor 104 and auditory prosthesis 110 via communication link 118. It will be understood that data communication link 118 may include a bi-directional communication link and/or one or more dedicated uni-directional communication links. In some alternative embodiments, sound processor 104 and auditory prosthesis 110 may be directly connected with one or more wires or the like.

Auditory prosthesis 110 may include any type of implantable stimulator that may be used in association with the systems and methods described herein. For example, auditory prosthesis 110 may include an implantable cochlear stimulator. In some alternative implementations, auditory prosthesis 110 may include a brainstem implant and/or any other type of auditory prosthesis that may be implanted within a patient and configured to apply stimulation to one or more stimulation sites located along an auditory pathway of a patient.

In some examples, auditory prosthesis 110 may be configured to generate electrical stimulation representative of an audio signal detected by microphone 102 in accordance with one or more stimulation parameters transmitted thereto by sound processor 104. Auditory prosthesis 110 may be further configured to apply the electrical stimulation to one or more stimulation sites within the patient via one or more electrodes 114 disposed along lead 112. In some examples, auditory prosthesis 110 may include a plurality of independent current sources each associated with a channel defined by one or more of electrodes 114. In this manner, different stimulation current levels may be applied to multiple stimulation sites simultaneously by way of multiple electrodes 114. In such examples, auditory prosthesis system 100 may be referred to as a "multi-channel auditory prosthesis system."

Figure 2:
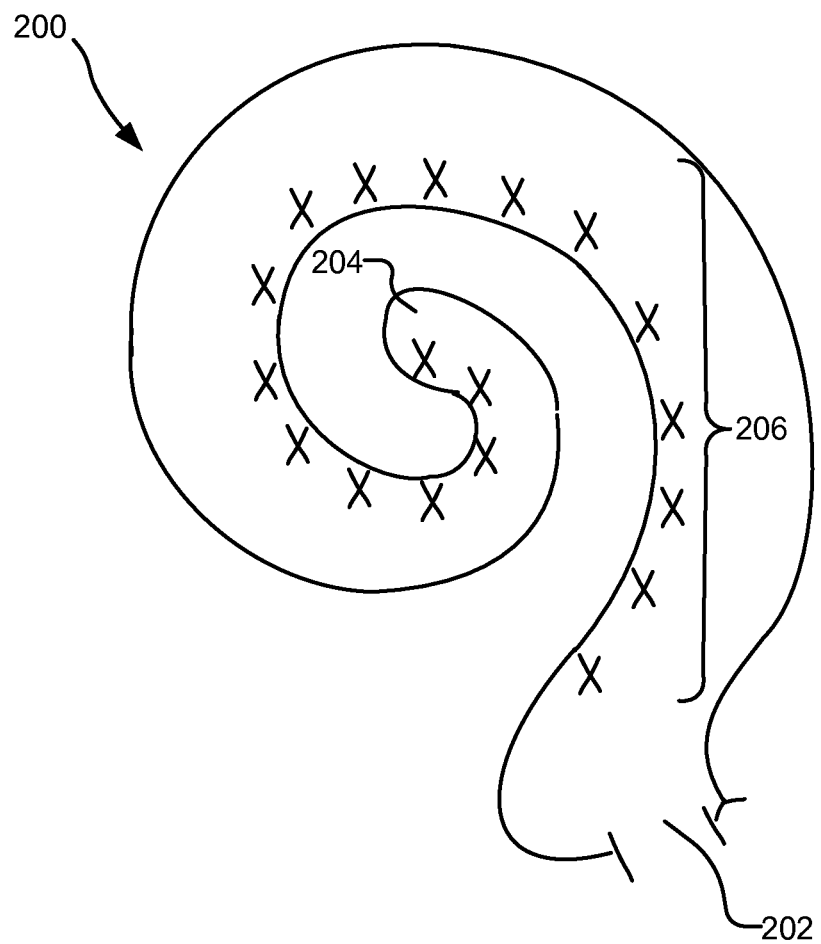
FIG. 2 illustrates a schematic structure of the human cochlea.

To facilitate application of the electrical stimulation generated by auditory prosthesis 110, lead 112 may be inserted within a duct of the cochlea such that electrodes 114 are in communication with one or more stimulation sites within the cochlea. FIG. 2 illustrates a schematic structure of the human cochlea 200 into which lead 112 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Low frequencies are encoded at the apex 204 of the cochlea 200 while high frequencies are encoded at the base 202. Hence, each location along the length of the cochlea 200 corresponds to a different perceived frequency. Auditory prosthesis system 100 may therefore be configured to apply electrical stimulation to different locations within the cochlea 200 (e.g., different locations along the auditory nerve tissue 206) to provide a sensation of hearing.

Alternatively, lead 112 may be implanted within a patient such that electrodes 114 are in communication with one or more stimulation sites otherwise located along the auditory pathway. As used herein, the term "in communication with" refers to electrodes 114 being adjacent to, in the general vicinity of, in close proximity to, directly next to, or directly on the stimulation site. Any number of electrodes 114 (e.g., sixteen) may be disposed on lead 112 as may serve a particular implementation.

Figure 3:
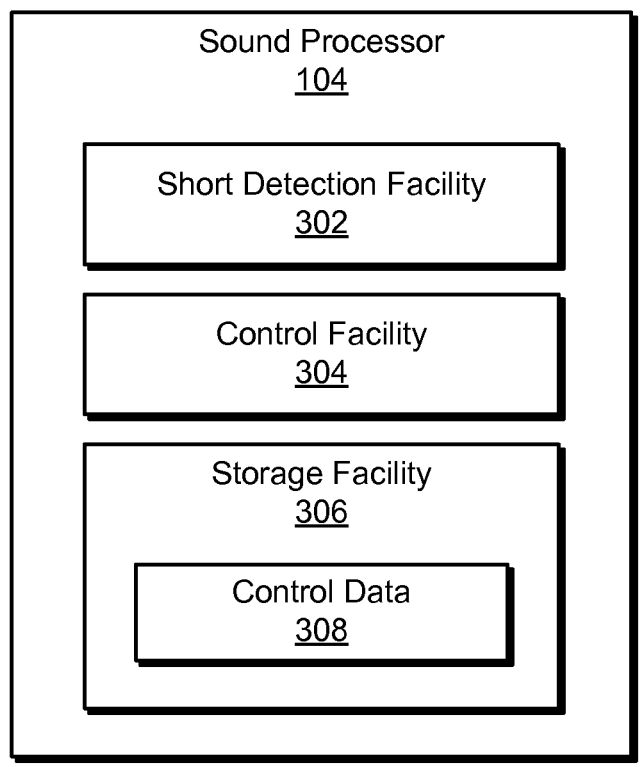
FIG. 3 illustrates exemplary components of a sound processor according to principles described herein.

FIG. 3 illustrates exemplary components of sound processor 104. It will be recognized that the components shown in FIG. 3 are merely representative of the many different components that may be included in sound processor 104 and that sound processor 104 may include additional or alternative components as may serve a particular implementation.

As shown in FIG. 3, sound processor 104 may include a short detection facility 302, a control facility 304, and a storage facility 306, which may be in communication with one another using any suitable communication technologies. Each of these facilities 302-306 may include any combination of hardware, software, and/or firmware as may serve a particular implementation. For example, one or more of facilities 302-306 may include a computing device or processor configured to perform one or more of the functions described herein. Facilities 302-306 will now be described in more detail.

Short detection facility 302 may be configured to determine that two or more electrodes 114 are shorted together. For example, short detection facility may determine that a first electrode and a second electrode are shorted together. It will be recognized that any subset of electrodes 114 may be shorted together for any reason.

Short detection facility 302 may determine that two or more electrodes 114 are shorted together in any suitable manner as may serve a particular implementation. For example, short detection facility 302 may determine that two or more electrodes 114 are shorted together based on impedance measurements of the electrodes, detected neural responses that occur as a result of electrical stimulation being delivered to one or more electrodes, and/or any other factor as may serve a particular implementation.

Control facility 304 may be configured to perform one or more operations associated with a control of auditory prosthesis 110. For example, once short detection facility 302 has determined that a first electrode and a second electrode are shorted together, control facility 304 may detect that a main electrical stimulation pulse intended only for the first electrode is to be delivered by auditory prosthesis 110 to the first electrode. To illustrate, control facility 304 may recognize that the main electrical stimulation pulse is about to be delivered to the first electrode in accordance with a particular sound processing strategy. However, because the first electrode and the second electrode are shorted together, delivery of the electrical stimulation pulse to the first electrode may cause an unwanted electrical stimulation pulse, which may be substantially similar to the main electrical stimulation pulse, to be simultaneously delivered to the second electrode.

In order to minimize the perceptual disturbance caused by the unwanted electrical stimulation pulse, control facility 304 may be further configured to direct, in response to the detection, auditory prosthesis 110 to concurrently deliver the main electrical stimulation pulse to the first electrode and one or more compensating electrical stimulation pulses to one or more additional electrodes included in electrodes 114. As will be described in more detail below, the one or more compensating electrical stimulation pulses are out-of-phase with respect to the unwanted electrical stimulation pulse and are configured to minimize the perceptual disturbance caused by the unwanted electrical stimulation pulse.

Storage facility 306 may be configured to maintain control data 308 (e.g., control parameters) utilized by control facility 304. Storage facility 306 may be configured to maintain additional or alternative data as may serve a particular implementation.

Figure 4:
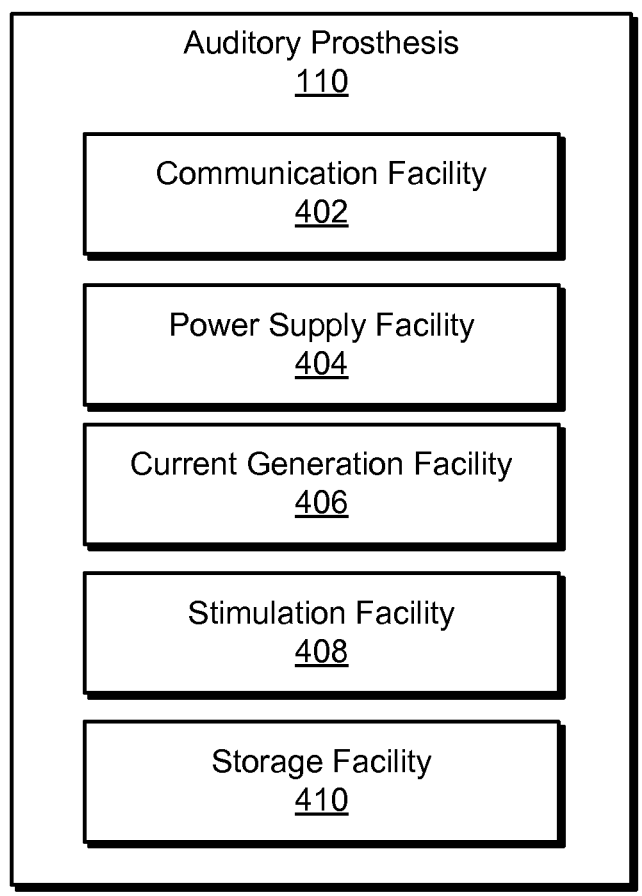
FIG. 4 illustrates exemplary components of an auditory prosthesis according to principles described herein.

FIG. 4 illustrates exemplary components of auditory prosthesis 110. As shown in FIG. 4, auditory prosthesis 110 may include a current generation facility 402, a stimulation facility 404, and a storage facility 406, which may be in communication with one another using any suitable communication technologies. Each of these facilities 402-406 may include any combination of hardware, software, and/or firmware as may serve a particular application. For example, one or more of facilities 402-406 may include a computing device or processor configured to perform one or more of the functions described herein. Facilities 402-406 will now be described in more detail.

Current generation facility 402 may be configured to generate stimulation current in accordance with one or more stimulation parameters received from sound processor 104.

To this end, current generation facility 402 may include one or more current generators and/or any other circuitry configured to facilitate generation of stimulation current. For example, current generation facility 402 may include an array of independent current generators each corresponding to a distinct electrode or channel.

Stimulation facility 404 may be configured to facilitate application of the stimulation current generated by current generation facility 402 to one or more stimulation sites within the patient in accordance with one or more stimulation parameters received from sound processor 104. For example, stimulation facility 402 may be configured to apply electrical stimulation pulses to one or more electrodes in accordance with one or more stimulation parameters provided by sound processor 102.

Storage facility 406 may be configured to maintain data generated and/or utilized by auditory prosthesis 110. For example, storage facility 406 may maintain data representative of one or more stimulation parameters configured to define the stimulation current generated and applied by auditory prosthesis 110.

Figure 5:
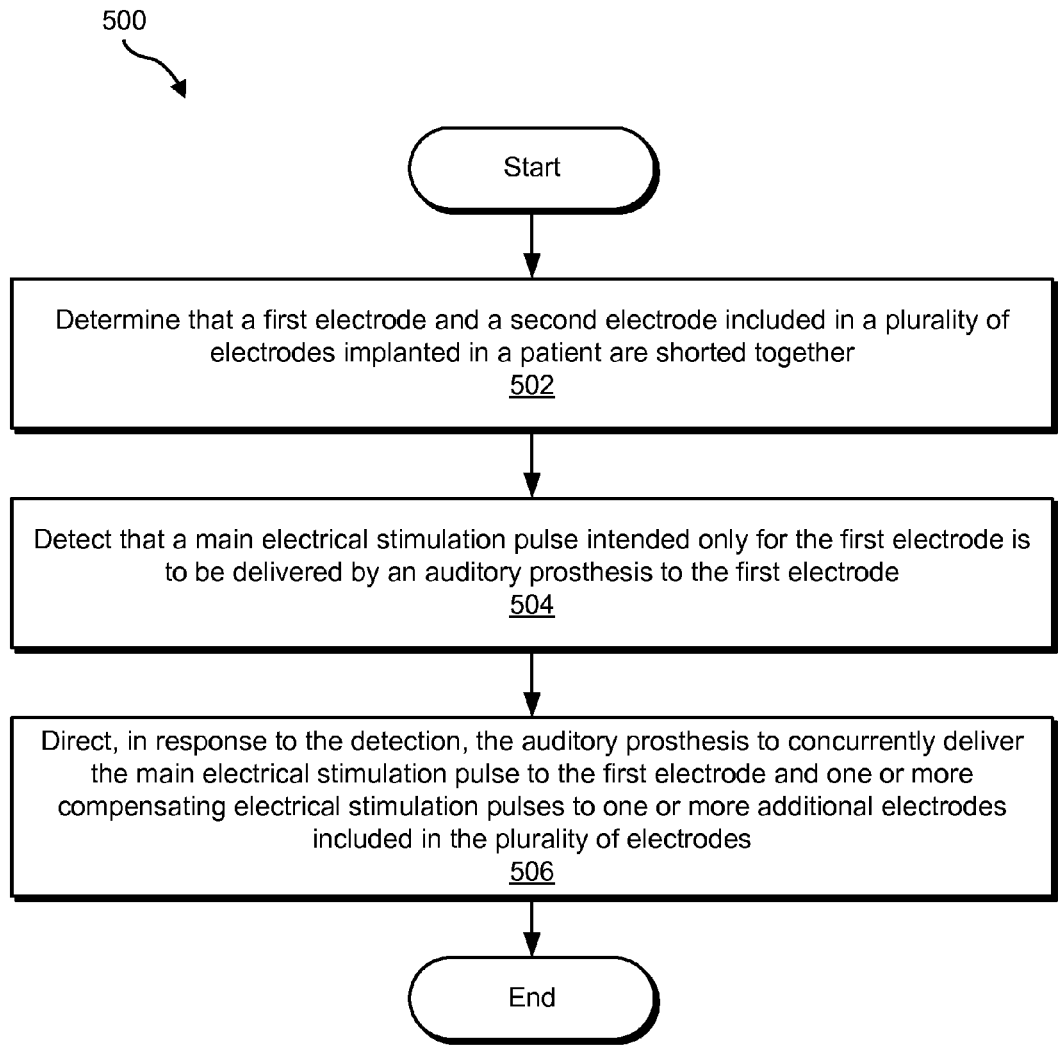
FIG. 5 illustrates an exemplary method of minimizing a perceptual disturbance caused by shorted electrodes in an auditory prosthesis system according to principles described herein.

FIG. 5 illustrates an exemplary method 500 of minimizing a perceptual disturbance caused by shorted electrodes in an auditory prosthesis system. While FIG. 5 illustrates exemplary steps according to one embodiment, other embodiments may omit, add to, reorder, and/or modify any of the steps shown in FIG. 5. One or more of the steps shown in FIG. 5 may be performed by any component or combination of components of sound processor 104.

Figure 6:
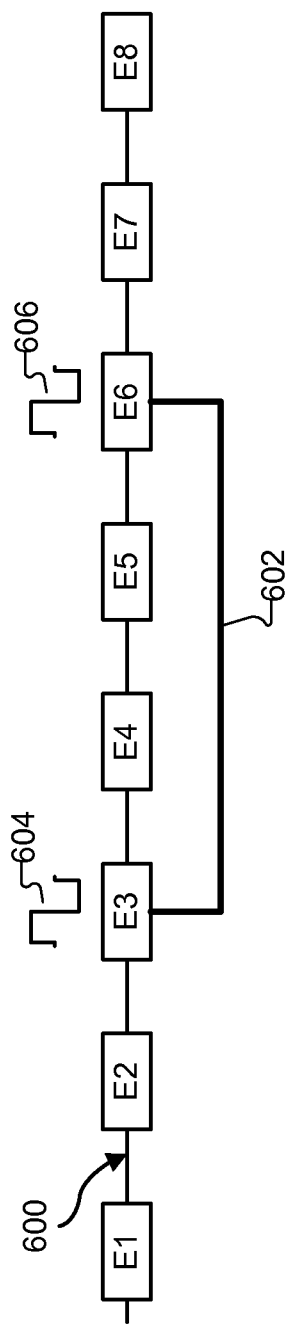
FIG. 6 shows an exemplary lead that may include a plurality of electrodes disposed thereon according to principles described herein.

In step 502, sound processor 104 determines that a first electrode and a second electrode included in a plurality of electrodes implanted in a patient are shorted together. To illustrate, FIG. 6 shows an exemplary lead 600 that may include a plurality of electrodes (e.g., electrodes E1 through E8) disposed thereon. While eight electrodes are shown to be disposed on lead 600 in FIG. 6, it will be recognized that lead 600 may alternatively include any other number of electrodes disposed thereon as may serve a particular implementation.

In some examples, lead 600 may be implanted within an auditory prosthesis patient and communicatively coupled to auditory prosthesis 110 such that auditory prosthesis 110 may deliver one or more electrical stimulation pulses to one or more of electrodes E1-E8. However, in some instances, two or more of electrodes E1-E8 may become shorted together. To illustrate, solid line 602 indicates that electrodes E3 and E6 have been shorted together. Sound processor 104 may determine that electrodes E3 and E6 are shorted together in any suitable manner, including any of the ways described herein.

Returning to FIG. 5, in step 504, sound processor 104 detects that a main electrical stimulation pulse intended only for the first electrode is to be delivered by auditory prosthesis 110 to the first electrode. For example, with reference again to FIG. 6, sound processor 104 may detect that a main electrical stimulation pulse 604 intended only for electrode E3 is to be delivered by auditory prosthesis 110 to electrode E3. However, as described above, because electrodes E3 and E6 are shorted together, delivery of electrical stimulation pulse 604 to electrode E3 may cause an unwanted electrical stimulation pulse 606 to be simultaneously delivered to electrode E6. As shown, unwanted electrical stimulation pulse 606 may be substantially similar to main electrical stimulation pulse 604. However, it will be recognized that unwanted electrical stimulation pulse 606 may differ from main electrical stimulation pulse 604 in any way.

Returning to FIG. 5, in step 506, sound processor 104 directs, in response to the detection performed in step 504, auditory prosthesis 110 to concurrently deliver the main electrical stimulation pulse to the first electrode and one or more compensating electrical stimulation pulses to one or more additional electrodes included in the plurality of electrodes.

Sound processor 104 may select the one or more additional electrodes to which the one or more compensating electrical stimulation pulses are delivered in accordance with any suitable selection heuristic. For example, sound processor 104 may deliver a single compensating electrical stimulation pulse to a single electrode that is adjacent to the second electrode (i.e., the shorted electrode to which the unwanted electrical stimulation pulse is delivered).

To illustrate, with reference again to FIG. 6, sound processor 104 may deliver a single compensating electrical stimulation pulse to electrode E7 in order to minimize a perceptual disturbance caused by the delivery of unwanted electrical stimulation pulse 606 to electrode E6. As shown, electrode E7 is adjacent to electrode E6. In other words, there are no electrodes disposed along lead 600 in between electrodes E6 and E7. It will be recognized that electrode E5 is also adjacent to electrode E6 and that it may alternatively be selected as the electrode to which the single compensating electrical stimulation pulse is delivered. In some examples, when there are two non-shorted electrodes adjacent to a shorted electrode, sound processor 104 may select the electrode (e.g., electrode E7) that is furthest away from the electrode to which the main electrical stimulation pulse is to be applied (e.g., electrode E3) as the compensating electrode. Hence, for illustrative purposes only, it will be assumed that the compensating electrical stimulation pulse is delivered to electrode E7 in the examples given herein.

The single compensating electrical stimulation pulse delivered to electrode E7 may be out-of-phase with respect to the unwanted electrical stimulation pulse 606 delivered to electrode E6. As used herein, a compensating electrical stimulation pulse that is "out-of-phase" with respect to an unwanted electrical stimulation pulse is one that is opposite in polarity to the unwanted electrical stimulation pulse such that when the compensating electrical stimulation pulse and the unwanted electrical stimulation pulse are concurrently delivered, the amplitude of the compensating electrical stimulation pulse effectively cancels out at least a portion of the amplitude of the unwanted electrical stimulation pulse.

Figure 7:
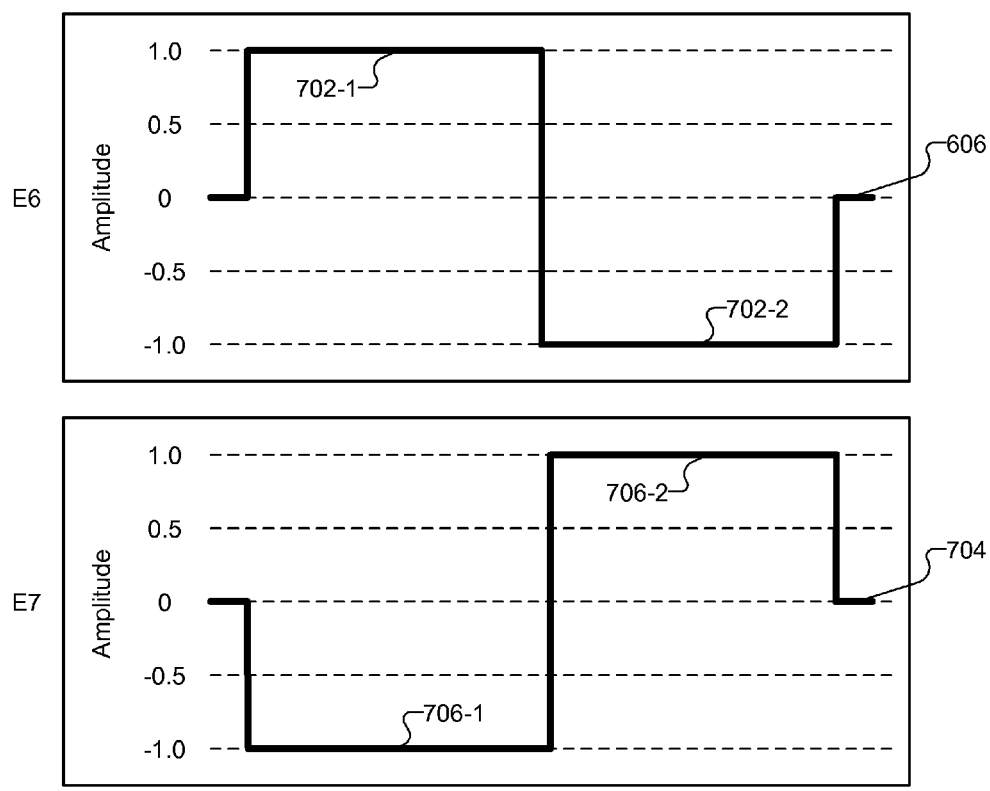
FIG. 7 shows an exemplary unwanted electrical stimulation pulse and an exemplary compensating electrical stimulation pulse according to principles described herein.

To illustrate, FIG. 7 shows the exemplary unwanted electrical stimulation pulse 606 that may be delivered to electrode E6 of FIG. 6. As shown, unwanted electrical stimulation pulse 606 may include a square wave with a first phase 702-1 having an amplitude of 1.0 followed by a second phase 702-2 having an amplitude of −1.0. It will be recognized that unwanted electrical stimulation pulse 606 may alternatively have any other type of shape and/or amplitude as may serve a particular implementation.

FIG. 7 also shows an exemplary compensating electrical stimulation pulse 704 that may be concurrently delivered to electrode E7. As shown, compensating electrical stimulation pulse 704 may include a square wave with a first phase 706-1 having an amplitude of −1.0 followed by a second phase 706-2 having an amplitude of 1.0. As shown in FIG. 7, compensating electrical stimulation pulse 704 is out-of-phase with respect to unwanted electrical stimulation pulse 606. In other words, the polarity of first phase 706-1 is opposite that of first phase 702-1 and the polarity of second phase 706-2 is opposite that of second phase 702-2. In this manner, concurrent delivery of compensating electrical stimulation pulse 704 and unwanted electrical stimulation pulse 606 may effectively cancel out at least a portion of unwanted electrical stimulation pulse 606 and thereby minimize a perceptual disturbance caused by the delivery of unwanted electrical stimulation pulse 606.

Another reason why compensating electrical stimulation pulse 704 may minimize a perceptual disturbance caused by the delivery of unwanted electrical stimulation pulse 606 is because the concurrent delivery of compensating electrical stimulation pulse 704 and unwanted electrical stimulation pulse 606 is performed in accordance with a bipolar stimulation strategy. As used herein, a "bipolar stimulation strategy" refers to any stimulation strategy in which two adjacent electrodes are concurrently stimulated. A "monopolar stimulation strategy," on the other hand, is one in which only a single electrode is stimulated. Hence, in the absence of compensating electrical stimulation pulse 704, delivery of unwanted electrical stimulation pulse 606 may be considered to be performed in accordance with a monopolar stimulation strategy. Relatively higher current levels are needed to achieve comfortably loud levels in bipolar stimulation strategies compared to monopolar stimulation strategies. Hence, concurrent delivery of compensating electrical stimulation pulse 704 may effectively reduce the loudness level associated with unwanted electrical stimulation pulse 606 and thereby minimize a perceptual disturbance caused by the delivery of unwanted electrical stimulation pulse 606.

Compensating electrical stimulation pulse 704 may have any suitable amplitude as may serve a particular implementation. For example, as shown in FIG. 7, compensating electrical stimulation pulse 704 may have an amplitude substantially equal to that of unwanted electrical stimulation pulse 606. In this manner, the loudness level of unwanted electrical stimulation pulse 606 may be effectively canceled out. However, it will be recognized that compensating electrical stimulation pulse 704 may have an amplitude less than that of unwanted electrical stimulation pulse 606 and still minimize a perceptual disturbance caused by the delivery of unwanted electrical stimulation pulse 606.

In some alternative examples, sound processor 104 may deliver compensating electrical stimulation pulses to two or more electrodes that surround the second electrode (i.e., the shorted electrode to which the unwanted electrical stimulation pulse is delivered). To illustrate, with reference again to FIG. 6, sound processor 104 may concurrently deliver a first compensating electrical stimulation pulse to electrode E5 and a second compensating electrical stimulation pulse to electrode E7 in order to minimize a perceptual disturbance caused by the delivery of unwanted electrical stimulation pulse 606 to electrode E6.

Figure 8:
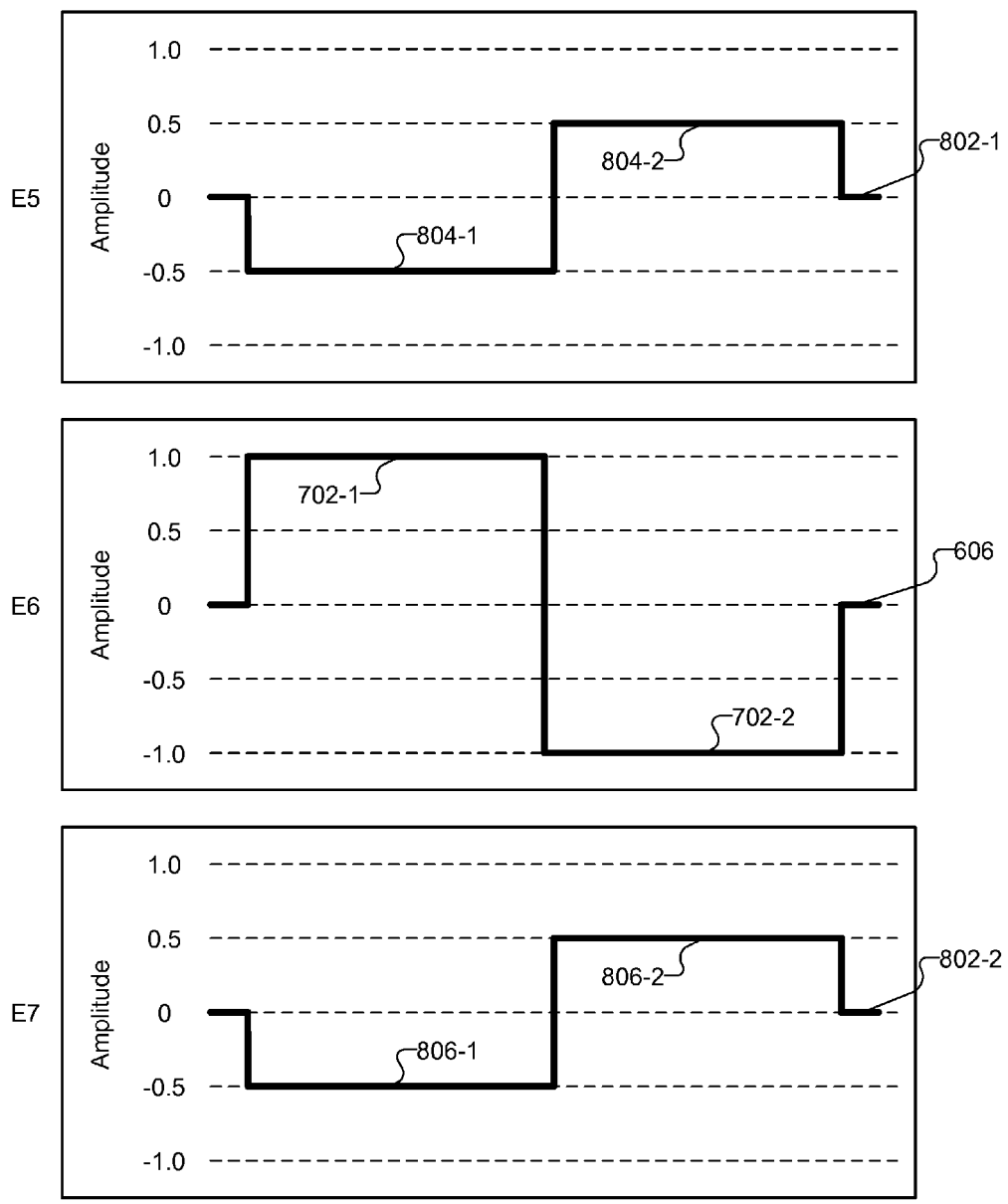
FIG. 8 shows an exemplary unwanted electrical stimulation pulse and two exemplary compensating electrical stimulation pulses according to principles described herein.

Both of the compensating electrical stimulation pulses delivered to electrodes E5 and E7 may be out-of-phase with respect to the unwanted electrical stimulation pulse delivered to electrode E6. To illustrate, FIG. 8 again shows unwanted electrical stimulation pulse 606 that may be delivered to electrode E6 of FIG. 6. FIG. 8 also shows a first compensating electrical stimulation pulse 802-1 and a second compensating electrical stimulation pulse 802-2 (collectively referred to herein as "compensating electrical stimulation pulses 802") that may be delivered to electrodes E5 and E7, respectively.

As shown, compensating electrical stimulation pulses 802 may each be out-of-phase with respect to unwanted electrical stimulation pulse 606. In other words, the polarity of the first phase (e.g., 804-1 and 806-1) of each compensating electrical stimulation pulse 802 is opposite that of first phase 702-1 of unwanted electrical stimulation pulse 606 and the polarity of the second phase (e.g., 804-2 and 806-2) of each compensating electrical stimulation pulse 802 is opposite that of second phase 702-2 of unwanted electrical stimulation pulse 606. In this manner, concurrent delivery of compensating electrical stimulation pulses 802 and unwanted electrical stimulation pulse 606 may effectively cancel out at least a portion of unwanted electrical stimulation pulse 606 and thereby minimize a perceptual disturbance caused by the delivery of unwanted electrical stimulation pulse 606.

The concurrent delivery of compensating electrical stimulation pulses 802 and unwanted electrical stimulation pulse 606 may be performed in accordance with a tripolar stimulation strategy. As used herein, a "tripolar stimulation strategy" refers to any stimulation strategy in which three adjacent electrodes are concurrently stimulated. As with bipolar stimulation strategies, relatively higher current levels are needed to achieve comfortably loud levels in tripolar stimulation strategies compared to monopolar stimulation strategies. Hence, concurrent delivery of compensating electrical stimulation pulses 802 may effectively reduce the loudness level associated with unwanted electrical stimulation pulse 606 and thereby minimize a perceptual disturbance caused by the delivery of unwanted electrical stimulation pulse 606.

Compensating electrical stimulation pulses 802 may have any suitable amplitude as may serve a particular implementation. For example, a combined amplitude of compensating electrical stimulation pulses 802 may be substantially equal to that of unwanted electrical stimulation pulse 606. To illustrate, FIG. 8 shows that each of compensating electrical stimulation pulses 802 may have an amplitude of 0.5. In this manner, the loudness level of unwanted electrical stimulation pulse 606 may be effectively canceled out. However, it will be recognized that compensating electrical stimulation pulses 802 may have a combined amplitude that is less than that of unwanted electrical stimulation pulse 606 and still minimize a perceptual disturbance caused by the delivery of unwanted electrical stimulation pulse 606.

It will be recognized that the examples given in connection with FIGS. 7 and 8 are merely illustrative and that compensating electrical stimulation pulses may be delivered to any number of other electrodes (e.g., in accordance with a multipolar stimulation strategy) in order to minimize a perceptual disturbance caused by the delivery of an unwanted electrical stimulation pulse. It will also be recognized that the electrodes to which the compensating electrical stimulation pulses are delivered do not necessarily have to be adjacent to the electrode(s) to which the unwanted electrical stimulation pulse is delivered.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory.

Common forms of computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other tangible medium from which a computer can read.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
   determining, by a sound processor communicatively coupled to an auditory prosthesis implanted in a patient, that a first electrode and a second electrode included in a plurality of electrodes implanted in the patient are shorted together;
   detecting, by the sound processor, that a main electrical stimulation pulse intended only for the first electrode is to be delivered by the auditory prosthesis to the first electrode; and
   directing, by the sound processor in response to the detecting, the auditory prosthesis to concurrently deliver the main electrical stimulation pulse to the first electrode and one or more compensating electrical stimulation pulses to one or more additional electrodes included in the plurality of electrodes;
   wherein the delivery of the main electrical stimulation pulse to the first electrode causes an unwanted electrical stimulation pulse to be simultaneously delivered to the second electrode; and
   wherein the one or more compensating electrical stimulation pulses are out-of-phase with respect to the unwanted electrical stimulation pulse and configured to minimize a perceptual disturbance caused by the unwanted electrical stimulation pulse.

2. The method of claim 1, wherein the one or more additional electrodes comprise a single electrode adjacent to the second electrode and wherein the one or more compensating electrical stimulation pulses comprise a single compensating electrical stimulation pulse delivered to the single electrode.

3. The method of claim 2, wherein an amplitude of the single compensating electrical stimulation pulse is substantially equal to an amplitude of the unwanted electrical stimulation pulse.

4. The method of claim 1, wherein the one or more additional electrodes comprise a third electrode and a fourth electrode each adjacent to the second electrode and wherein the one or more compensating electrical stimulation pulses comprise a first compensating electrical stimulation pulse delivered to the third electrode and a second compensating electrical stimulation pulse delivered to the fourth electrode.

5. The method of claim 4, wherein a combined amplitude of the first and second compensating electrical stimulation pulses is substantially equal to an amplitude of the unwanted electrical stimulation pulse.

6. The method of claim 1, wherein the one or more additional electrodes are selected based on a distance of the one or more electrodes from the second electrode.

7. The method of claim 1, further comprising:
   detecting, by the sound processor, that an additional main electrical stimulation pulse intended only for the second electrode is to be delivered by the auditory prosthesis to the second electrode; and
   directing, by the sound processor in response to the detecting that the additional main electrical stimulation pulse is to be delivered to the second electrode, the auditory prosthesis to concurrently deliver the additional main electrical stimulation pulse to the second electrode and an additional compensating electrical stimulation pulse to a third electrode included in the plurality of electrodes;
   wherein the delivery of the additional main electrical stimulation pulse to the second electrode causes an additional unwanted electrical stimulation pulse to be simultaneously delivered to the first electrode; and
   wherein the additional compensating electrical stimulation pulse is out-of-phase with respect to the additional unwanted electrical stimulation pulse and configured to minimize a perceptual disturbance caused by the additional unwanted electrical stimulation pulse.

8. The method of claim 1, wherein the auditory prosthesis comprises a cochlear implant.

9. The method of claim 1, embodied as computer-executable instructions on at least one non-transitory computer-readable medium.

10. A sound processor comprising:
    a short detection facility configured to determine that a first electrode and a second electrode included in a plurality of electrodes implanted in an auditory prosthesis patient are shorted together; and
    a control facility communicatively coupled to the short detection facility and configured to
       detect that a main electrical stimulation pulse intended only for the first electrode is to be delivered to the first electrode, and
       direct, in response to the detection, an auditory prosthesis implanted in the patient to concurrently deliver the main electrical stimulation pulse to the first electrode and one or more compensating electrical stimulation pulses to one or more additional electrodes included in the plurality of electrodes;
    wherein the delivery of the main electrical stimulation pulse to the first electrode causes an unwanted electrical stimulation pulse to be simultaneously delivered to the second electrode; and
    wherein the one or more compensating electrical stimulation pulses are out-of-phase with respect to the unwanted electrical stimulation pulse and configured to minimize a perceptual disturbance caused by the unwanted electrical stimulation pulse.

11. The sound processor of claim 10, wherein the one or more additional electrodes comprise a single electrode adjacent to the second electrode and wherein the one or more compensating electrical stimulation pulses comprise a single compensating electrical stimulation pulse delivered to the single electrode.

12. The sound processor of claim 11, wherein an amplitude of the single compensating electrical stimulation pulse is substantially equal to an amplitude of the unwanted electrical stimulation pulse.

13. The sound processor of claim 10, wherein the one or more additional electrodes comprise a third electrode and a fourth electrode each adjacent to the second electrode and wherein the one or more compensating electrical stimulation pulses comprise a first compensating electrical stimulation pulse delivered to the third electrode and a second compensating electrical stimulation pulse delivered to the fourth electrode.

14. The sound processor of claim 13, wherein a combined amplitude of the first and second compensating electrical stimulation pulses is substantially equal to an amplitude of the unwanted electrical stimulation pulse.

15. The sound processor of claim 10, wherein the control facility is further configured to
    detect that an additional main electrical stimulation pulse intended only for the second electrode is to be delivered by the auditory prosthesis to the second electrode, and
    direct, in response to the detecting that the additional main electrical stimulation pulse is to be delivered to the second electrode, the auditory prosthesis to concurrently deliver the additional main electrical stimulation pulse to the second electrode and an additional compensating electrical stimulation pulse to a third electrode included in the plurality of electrodes;
    wherein the delivery of the additional main electrical stimulation pulse to the second electrode causes an additional unwanted electrical stimulation pulse to be simultaneously delivered to the first electrode; and
    wherein the additional compensating electrical stimulation pulse is out-of-phase with respect to the additional unwanted electrical stimulation pulse and configured to minimize a perceptual disturbance caused by the additional unwanted electrical stimulation pulse.

16. The sound processor of claim 10, wherein the auditory prosthesis comprises a cochlear implant.

17. An auditory prosthesis system comprising:
    an auditory prosthesis configured to be implanted within a patient and communicatively coupled to a plurality of electrodes; and
    a sound processor communicatively coupled to the auditory prosthesis and configured to
        determine that a first electrode and a second electrode included in the plurality of electrodes implanted in the patient are shorted together,
        detect that a main electrical stimulation pulse intended only for the first electrode is to be delivered to the first electrode, and
        direct, in response to the detection, the auditory prosthesis to concurrently deliver the main electrical stimulation pulse to the first electrode and one or more compensating electrical stimulation pulses to one or more additional electrodes included in the plurality of electrodes;
    wherein the delivery of the main electrical stimulation pulse by the auditory prosthesis to the first electrode causes an unwanted electrical stimulation pulse to be simultaneously delivered to the second electrode; and
    wherein the one or more compensating electrical stimulation pulses are out-of-phase with respect to the unwanted electrical stimulation pulse and configured to minimize a perceptual disturbance caused by the unwanted electrical stimulation pulse.

18. The system of claim 17, wherein the one or more additional electrodes comprise a single electrode adjacent to the second electrode and wherein the one or more compensating electrical stimulation pulses comprise a single compensating electrical stimulation pulse delivered to the single electrode.

19. The system of claim 18, wherein an amplitude of the single compensating electrical stimulation pulse is substantially equal to an amplitude of the unwanted electrical stimulation pulse.

20. The system of claim 17, wherein the one or more additional electrodes comprise a third electrode and a fourth electrode each adjacent to the second electrode and wherein the one or more compensating electrical stimulation pulses comprise a first compensating electrical stimulation pulse delivered to the third electrode and a second compensating electrical stimulation pulse delivered to the fourth electrode.

* * * * *